US010001313B2

(12) United States Patent
Petrov

(10) Patent No.: US 10,001,313 B2
(45) Date of Patent: Jun. 19, 2018

(54) REUSABLE CRYOGENIC CARRYING CASE FOR BIOLOGICAL MATERIALS

(71) Applicant: Stan C. Petrov, Newport Beach, CA (US)

(72) Inventor: Stan C. Petrov, Newport Beach, CA (US)

(73) Assignee: INOVATZIA, INC., Irvine, CA (US)

( * ) Notice: Subject to any disclaimer, the term of this patent is extended or adjusted under 35 U.S.C. 154(b) by 793 days.

(21) Appl. No.: 14/021,142

(22) Filed: Sep. 9, 2013

(65) Prior Publication Data

US 2015/0068232 A1    Mar. 12, 2015

(51) Int. Cl.
*F25J 3/00* (2006.01)
*B65B 63/08* (2006.01)
(Continued)

(52) U.S. Cl.
CPC .......... *F25D 3/107* (2013.01); *A01N 1/0257* (2013.01); *F25D 29/001* (2013.01);
(Continued)

(58) Field of Classification Search
CPC ...... A61F 2/062; A61F 2/30942; F25D 3/107; A01N 1/0268; A01N 1/0273;
(Continued)

(56) References Cited

U.S. PATENT DOCUMENTS 3,728,187 A * 4/1973 Martin ................... B29C 53/66
138/144
4,332,136 A * 6/1982 Quack .................... F25B 25/00
220/749
(Continued)

FOREIGN PATENT DOCUMENTS

EP          2647931 A1 * 10/2013    ............... F25D 3/10
WO    WO 9620379 A1 * 7/1996    ............. F25B 45/00

OTHER PUBLICATIONS

Translation of European Patent Document EP 2647931 A1 entitled EP 2647931 A1—Translation.*
(Continued)

*Primary Examiner* — Len Tran
*Assistant Examiner* — Paul Alvare

(57) ABSTRACT

A compact, mobile communicating carrying case for the transport and storage of temperature-sensitive materials. The carrying case regulates to temperature presets that can be altered real time directly or remotely. Cryogenic temperature control is provided by use of a low boiling point liquid coolant, like liquid nitrogen or air that accelerates in a multicore cooling system. A microprocessor-controlled double function solenoid acting as a valve and sensor, temperature sensors, and several mechanical one way release valves regulate the cooling system. Peripheral integrated modules collect, send, receive and display information on the case and on smart devices about location, core temperature, the carrier and the nature of the enclosed material. The carrying case provides a compact laser-etched sterile working area, in addition to a set of basic instruments, needed for procedures using the biological materials.

9 Claims, 16 Drawing Sheets

(51) Int. Cl.
| | |
|---|---|
| *F25D 23/12* | (2006.01) |
| *F25D 3/02* | (2006.01) |
| *F17C 1/00* | (2006.01) |
| *F17C 3/00* | (2006.01) |
| *F17C 13/00* | (2006.01) |
| *F25D 3/10* | (2006.01) |
| *F25D 29/00* | (2006.01) |
| *A01N 1/02* | (2006.01) |
| *F17C 13/02* | (2006.01) |

(52) U.S. Cl.
CPC .......... *A01N 1/0268* (2013.01); *A01N 1/0273* (2013.01); *F17C 13/025* (2013.01); *F17C 2205/0338* (2013.01); *F17C 2205/0391* (2013.01)

(58) Field of Classification Search
CPC ...... F17C 2205/0338; F17C 2205/0391; F17C 13/025
USPC .......... 606/132; 83/332; 600/36; 62/60, 337, 62/457.9, 463, 657; 220/560.1, 560.14
See application file for complete search history.

(56) References Cited

U.S. PATENT DOCUMENTS

| | | | |
|---|---|---|---|
| 4,739,622 A | 4/1988 | Smith | |
| 5,355,684 A * | 10/1994 | Guice | A01N 1/02 62/457.2 |
| 6,094,921 A * | 8/2000 | Zhu | F25B 9/145 60/520 |
| 6,226,997 B1 | 5/2001 | Vago | |
| 6,378,314 B1 * | 4/2002 | Clark | F17C 3/10 62/457.9 |
| 8,294,849 B2 | 10/2012 | Toko | |
| 2007/0183974 A1 | 8/2007 | Pearlman | |
| 2009/0133411 A1 | 5/2009 | Cheng | |
| 2010/0256622 A1 * | 10/2010 | Baust | A61B 18/02 606/23 |
| 2011/0022532 A1 | 1/2011 | Kriss | |
| 2012/0063973 A1 * | 3/2012 | Ang | A61J 1/10 422/555 |
| 2012/0067133 A1 * | 3/2012 | Waldrop | G01L 19/0015 73/753 |
| 2014/0069119 A1 * | 3/2014 | Katkov | F25D 3/10 62/51.1 |

OTHER PUBLICATIONS

International Search Report and Written Opinion of the International Searching Authority, International Application No. PCT/US14/54128, US Searching Authority, dated Feb. 2015, 15 pages.

\* cited by examiner

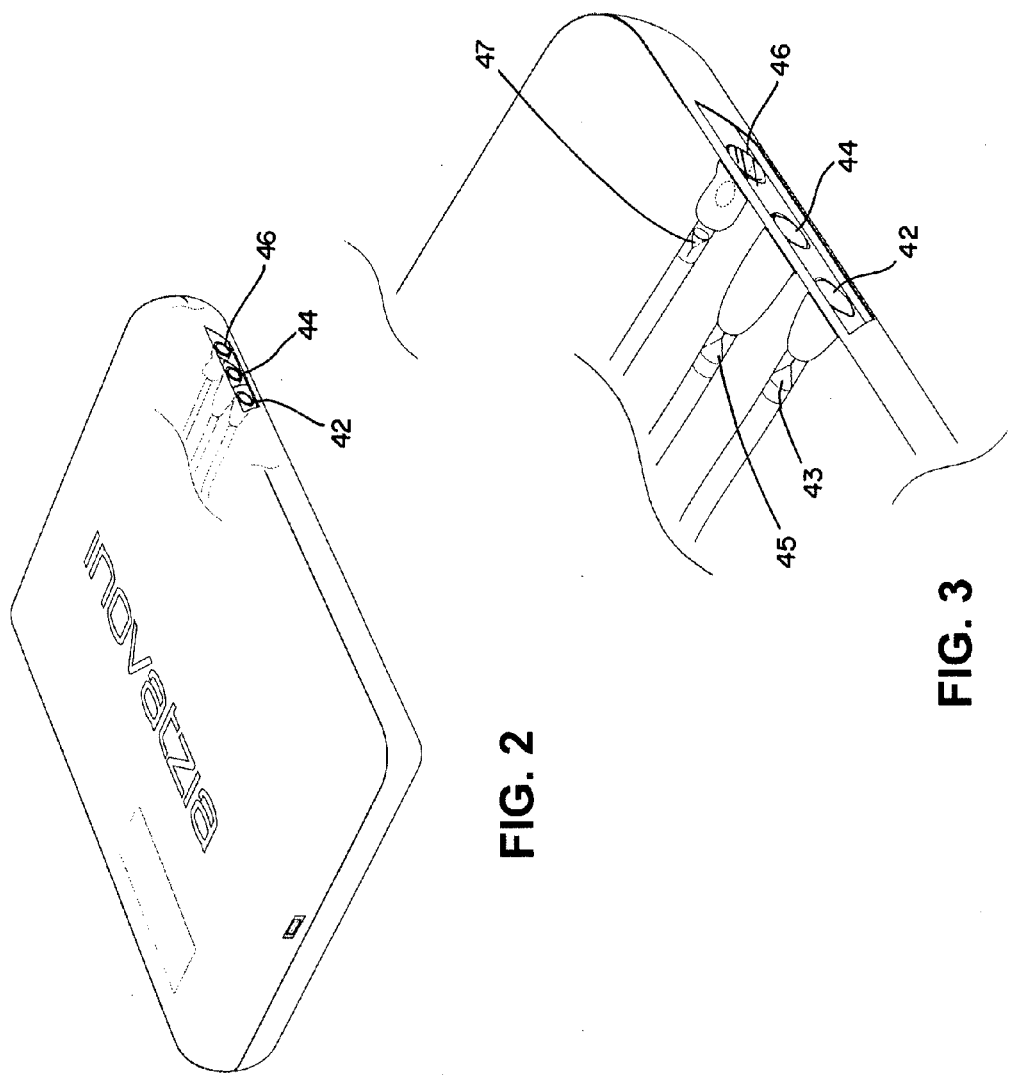

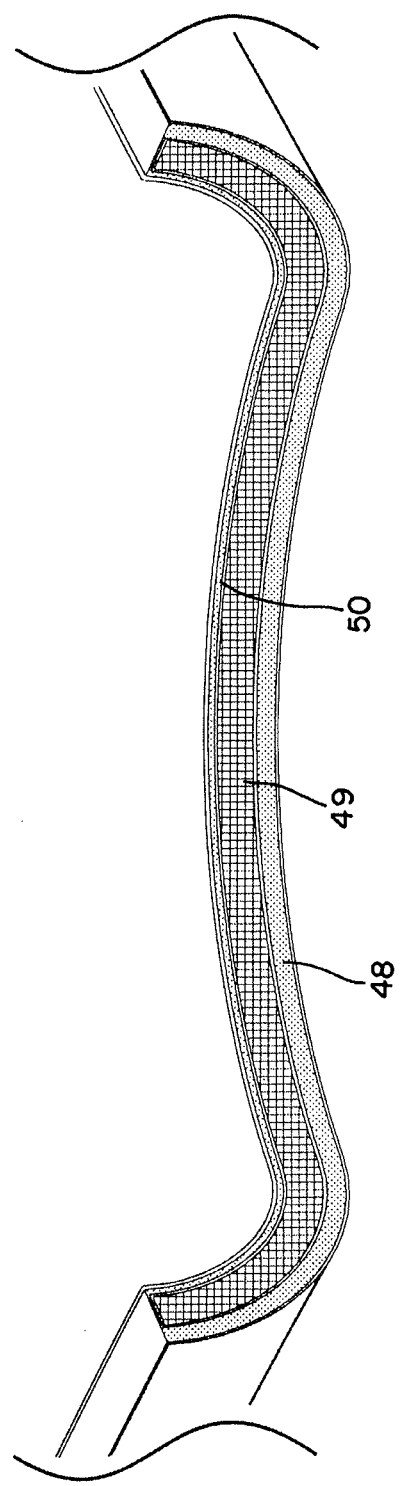

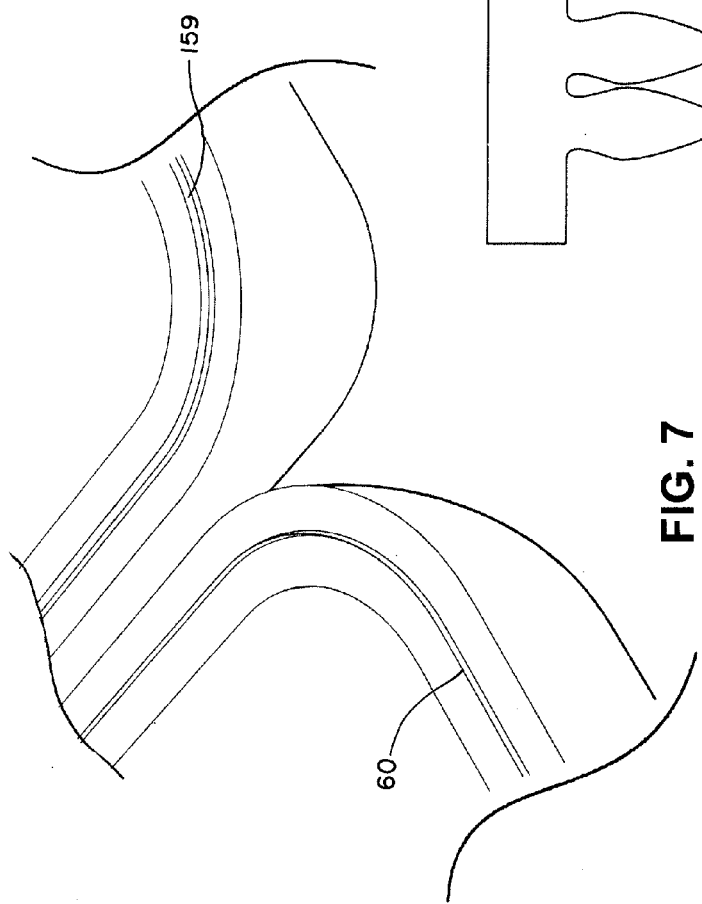
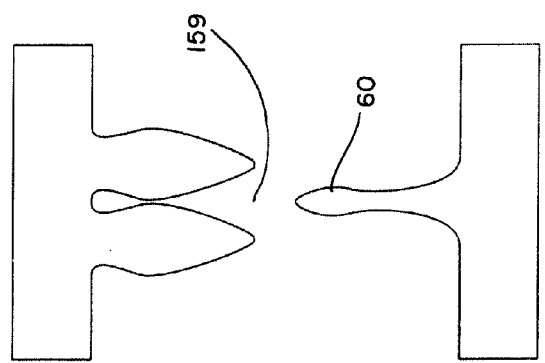
FIG. 7
FIG. 8

REUSABLE CRYOGENIC CARRYING CASE FOR BIOLOGICAL MATERIALS

BACKGROUND OF THE INVENTION

1. Field of the Invention

The present invention relates to a portable cryogenic carrying case for biological material that is capable of communicating.

2. Description of Related Art

The FDA recently approved the use of bone grafts, mesenchymal cells, umbilical stem cells, and skin grafts for clinical trials or use in the treatment of many conditions. Transplantation medicine is gaining in popularity as research snowballs and brings the potential advantages of this innovative approach forward. This is the time for development of new and better technologies that streamline the process for production of biomaterials (often consisting of cells to be used in grafting).

Unfortunately, the technology involved in the production and distribution of the biomaterials has not kept pace with the biotechnical advances. Currently, it is normal practice for biomaterials, such as named above, to be transported on dry ice by a distribution company and then frozen at −80° C. or in liquid nitrogen by the purchasing facility, until they are used. The distribution company often supplies these freezers, at great expense to the medical facility. At each stage of transport, the shipment is checked manually, as nurses check boxes on a form, and sometimes even by computer. Full knowledge of what is happening to the biomaterials is woefully deficient. The transport container is only for transport and does nothing to facilitate the use of the biomaterial.

There are difficulties with every stage in the transport and use of biomaterials. For example, shipping biomaterials on dry ice (−78° C.) by FedEx is costly and requires one-time use containers. Although there is a record of where the biomaterials were and for how long, there is no way to know whether they were kept at the required temperature. In addition, there is no record of their transport from the cell production facility to the manufacturer. Suboptimal temperatures are harmful to biologicals. Once the biomaterial arrives at its destination, medical personnel must transfer the biomaterial from the dry ice to a −80° C. freezer or liquid nitrogen tank without delay. More often than not, this vital step can be overlooked in a busy hospital. Moreover, since the freezer will contain other specimens, it is possible that an older shipment becomes confused with a newer one. Cells have a limited shelf life, which reduces the viability of the biomaterial graft and the chances that it will "take." It is even possible that inadequate labeling may result in biomaterials from one patient being transferred into another, potentially causing a catastrophic immune reaction. Surgery or implantation of the biomaterial is often less than straightforward. The medical facility must have the requisite sterile instruments and working surfaces on hand. The biomaterial, which has been removed from the freezer to be ready for use, could become too warm due to delays, causing loss of cell viability and denaturation of growth factors. For this reason, some distributors have personnel wait in the room ready for the surgery to be performed until the biomaterial is developed. This is a very expensive and highly inconvenient.

Even with these labor intensive procedures, graft failure is common. Some of the leading causes of failure are hematoma formation, which can be avoided by meshing of the biomaterial, infection, which can be reduced by meticulous preparation of the area, and surgeon error in placing the biomaterial upside down.

These are factors that the current systems of transport and delivery cannot address. The present invention, on the other hand, does. The communicating carrying case of the present invention reduces many risk factors that cause biomaterial failure in skin grafts, for example.

SUMMARY OF THE INVENTION

A mobile, compact, reusable carrier that is able to regulate its internal low temperature using an internal microcontrolled multicore pressure system, simplifies transportation and storage of biomaterials.

An inbuilt sterile instrument case with a work area, provides an operator with a useful tool that increases ease of care during a procedure. Grafts can fail due to hematoma, inadequate wound preparation and infection. The carrying case has a set of sterile surgical tools for fenestrating the grafts and biomaterials and reducing the likelihood of hematoma. The surgeon operator has everything needed in the case to thoroughly prepare a wound site.

The risks inherently associated with inadequate preparation of surgical trays due to operator error or even malfunctioning sterilization equipment is prevented. The inevitable infection risk associated with having an extra person scrub in (the person from the biomaterial manufacturer) will be avoided. The carrying case has a pouch adjacent to the surgical tools where the biomaterial is placed right side up, making correct placement obvious to the surgeon. The ID of the biomaterial is read during placement or removal by, for example, an RFID.

A microcontroller combined with sensors, a communication board, an ID reader, such as a radio frequency identification module ID, a built-in display, and other peripherals in the carrying case enable it to interact with its environment. It collects real time data such as the temperature of the biomaterial, the contents of the case, its location, a log of how long the material has been in transit and where it has been. The data gathered is available and communicated to the user, the transport company, the biomaterial manufacturer, or any other interested party.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein:

FIG. 2 is a back perspective of the carrying case;

FIG. 3 is an enlarged perspective illustration of three ports located at the back of the carrying case;

FIG. 4 is a cross-section of the case, showing the multilayer structure of the case;

FIG. 7 illustrates the seals located around the perimeter in the top and bottom of the carrier case;

FIG. 8 is a cross-section of the top and bottom seal showing how they interconnect;

DETAILED DESCRIPTION OF THE PREFERRED EMBODIMENTS

Figure 1:
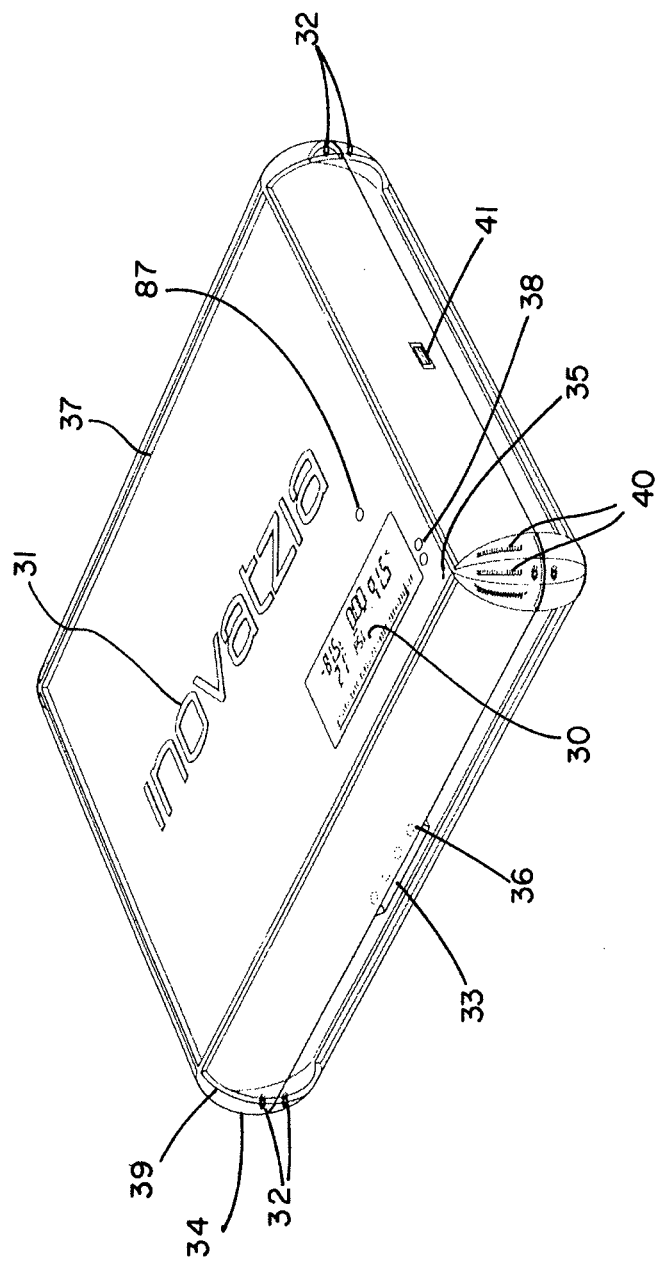
FIG. 1 is a front prospective of the outside of the carrying case.

A preferred embodiment of the outside of the cryogenic communicating carrying case, is shown in FIG. 1. A screen of multiple LEDs 30 that can be programmed to display various user-preferred information such as the contents of the case, or the temperature is located on the top. This screen has a non-thermoconductive protecting layer on the inside in order to allow it to function at low temperatures, as well as to prevent heat exchange between the external environment and the inside of the case. The logo 31 on the surface of the case is made of a temperature-sensitive material, so that it can act as a warning that the case is being exposed to excessive heat.

The top and bottom of the case close at the front and are held together by permanent magnets 32 at all four corners 34. A wedge-shaped indentation 33 on the bottom part of the case allows easy opening of the case. One of the magnets in one of the corners of the case is paired with a magnetic switch sensor (not shown) that sends a signal to a microcontroller (described hereinafter), registering if the case is open or closed. The corners of the case 34 are semitransparent to allow light produced by LEDs 35 on the top of the case to propagate to the bottom. A strip 36 of high brightness LEDs is located on the top at the latch area 33, to illuminate the latch area.

The semitransparent corners 34 of the case have built in reflectors. The corners are interconnected by a fiberoptic strip 37. The bottom right corner of the case contains multiple diodes such as infrared receivers, IR transmitters, and triple color high power LEDs 38. These diodes are surface mounted on a printed circuit board (PCB). The light signals from these diodes are transmitted to the other corners via the fiberoptic strip 37 and reflected by the reflectors 39 in each corner. This light signal is transmitted between the top and bottom of the case by way of two pieces of fiberoptics enclosed in small transparent areas at each corner of the case that meet when the case is closed. A GPS and Wifi antenna is located in the bottom right reflector 40. A USB slot 41 is provided to allow added communication capabilities.

Referring now to FIGS. 2 and 3, there are three conical openings in the back of the case (FIG. 3). An inlet 42 with a one way valve 43 enables charging the refrigeration system of the case with coolant such as liquid nitrogen, for example. An outlet 44 with a one way outlet valve 45 to enable continuous recirculation of nitrogen when long-term storage is desired. An exhaust 46 with an adjustable flow-limited pressure valve 47 enables release of excess nitrogen from the case. For safety, the exhaust tip of the exhaust 46 points towards the floor (not shown). The function of these one way valves will be discussed more fully hereinafter.

The top and bottom of the case is constructed from a multiple layer material, an example of which is shown in FIG. 4. An infrared-blocking molded thermal film 48 is used as an outside layer. A non-thermoconductive inner layer 49, such as zirconium, for example, is sandwiched by an inside reflective layer 50. This multilayer structure enables the carrier enclosure to act as a non-thermoconductive barrier between the outside and the inside of the case.

Figure 5:
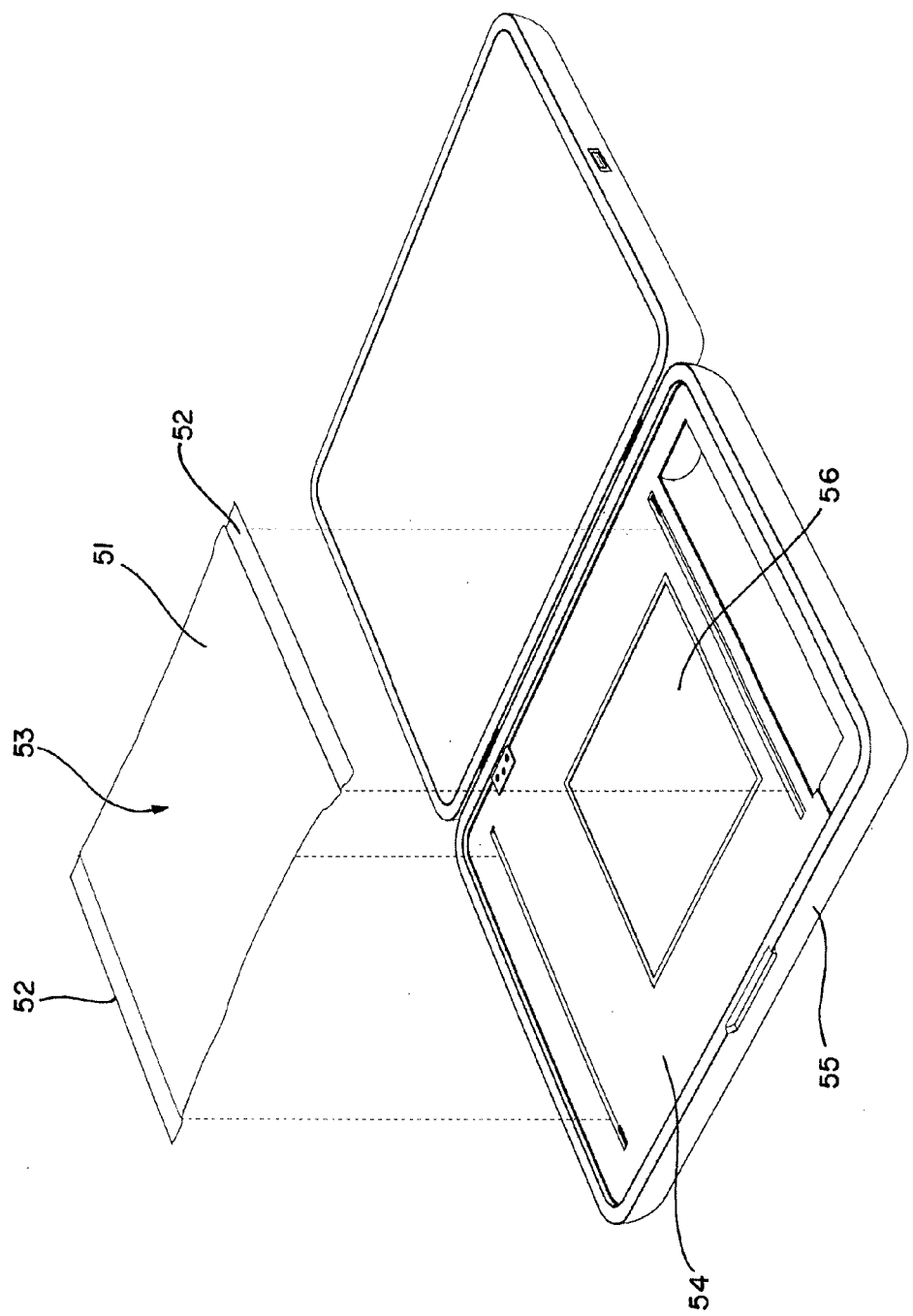
FIG. 5 is a front perspective of the case with the top opened, showing the bottom part with an exploded view of a biomaterial and ID-containing pouch.

FIG. 5 shows an open carrying case, revealing the inside surface of the bottom 55. A graft pouch 51 is shown in exploded view. A skin graft or other biomaterial frozen in its transport media, is enclosed within the reusable pouch 51 which has tabs 52 on either side. A non-thermoconductive removable film 53 covers the top of the pouch. A thin thermoconductive silver-based silicone/graphite gel (not shown) is on the bottom of the pouch. The graft pouch 51 rests on a base plate 54 in the bottom of the case. It is centered over an opening in the base plate 54 that is directly over the cooling inner core 56 below the base plate. The pouch is in direct contact with the cooling core when inside the case. The core will be described hereinafter.

Figure 6:
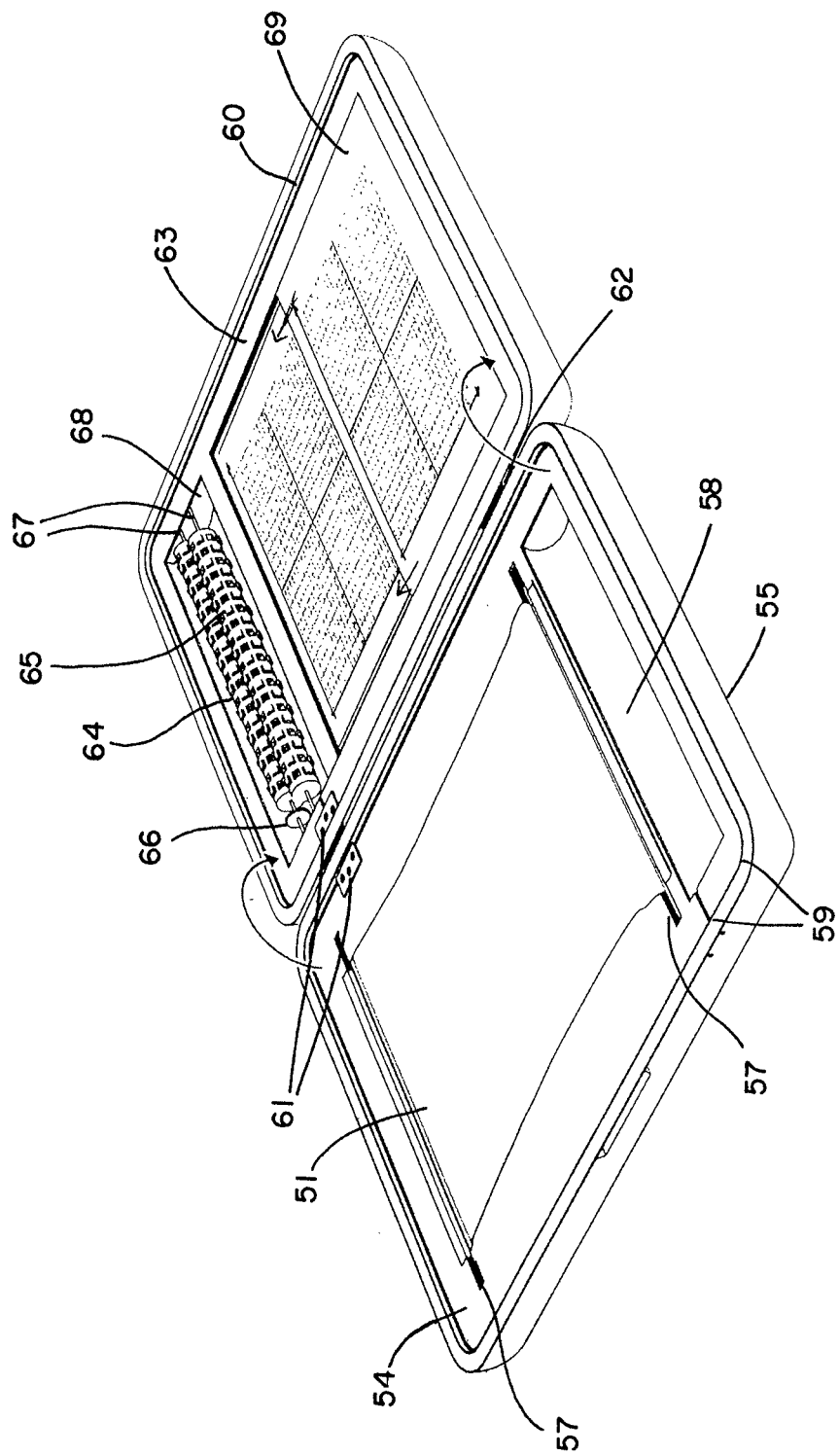
FIG. 6 is a back perspective of an open carrying case showing inner working surfaces or plates and the biomaterial-containing pouch.

FIG. 6 shows an open cryogenic carrying case showing the working surfaces contained inside. The graft pouch 51 is held in place on the base plate 54 in the bottom half of the case by two spring-loaded shafts 57 attached to the base plate, for easy release. The base plate contains a basin 53 for washing the biomaterial. A gutter system 59 encircles the entire base plate for collecting and returning spilled liquid to the basin 53. When the case is closed, the gutter 59 is enclosed in the case by a silicone seal 60. A spring ball-loaded magnetic connector 61 located near the hinges 62 allows a microcontroller in the top of the case to communicate with peripheral devices in the bottom (as described hereinafter).

A plate 63 in the top of the case contains all that an operator requires for accurate, effective, and sterile handling of the biomaterial. An indentation in the top plate 64 contains a drum graft mesher 65, which is used to fenestrate the biomaterial. The graft mesher 65 has a roller wheel 66 attached. This allows physical rotation of the drums. The mesher is held in place by spring-loaded clips at the end of shafts 67, for easy removal and cleaning. The fenestrated biomaterial feeds into a collecting basin 68 that is usually filled with fluid to avoid drying and tearing of the fragile tissue.

FIGS. 7 and 8 illustrate the gas and fluid impervious seal used in the cryogenic carrying case. The seal traverses the perimeters of the top and bottom, of the case. The seal has two parts. One part 60 is in the top of the case. The other part 159 is in the bottom of the case. The top seal 60 slides into the bottom seal 159 as shown in FIG. 8.

Figure 9:
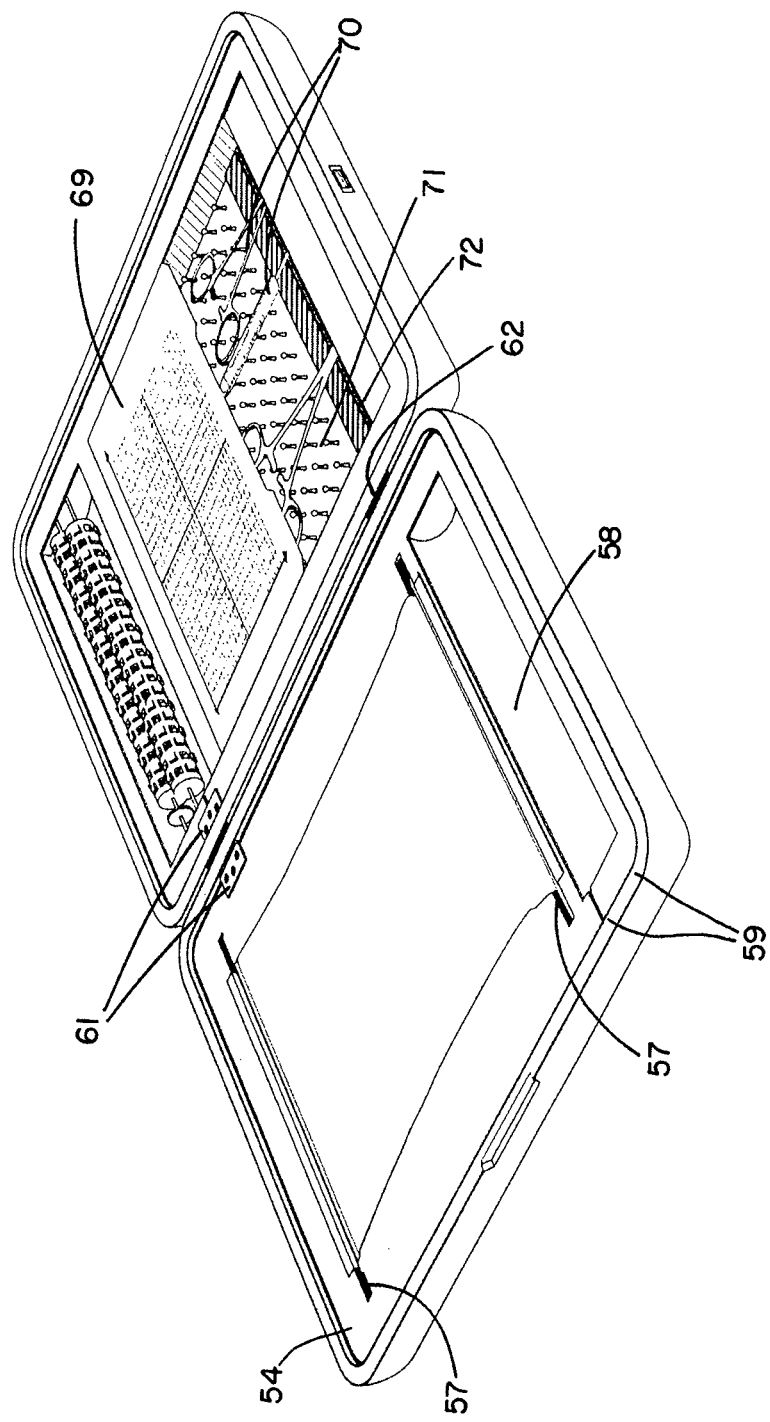
FIG. 9 is a perspective of an open carrying case showing contents of the top as having a working surface, a plate, a clean area, and an instrument compartment.

Referring now to FIG. 8, an instrument cover 69 and plate is laser-engraved with a grid that acts as a measuring tool, for use when cutting a biomaterial to size. This also provides an additional sterile working surface. When the instrument cover 69 is closed, as shown in FIG. 6, the surgeon operator has a large clean area on which to manipulate the biomaterial. When the working surface slides back (as shown in FIG. 9) access is provided to sterile instruments 70 underneath, nestled on a soft silicone cone-shaped mat 71 held in place by an embedded magnetic strip 72.

Figure 10:
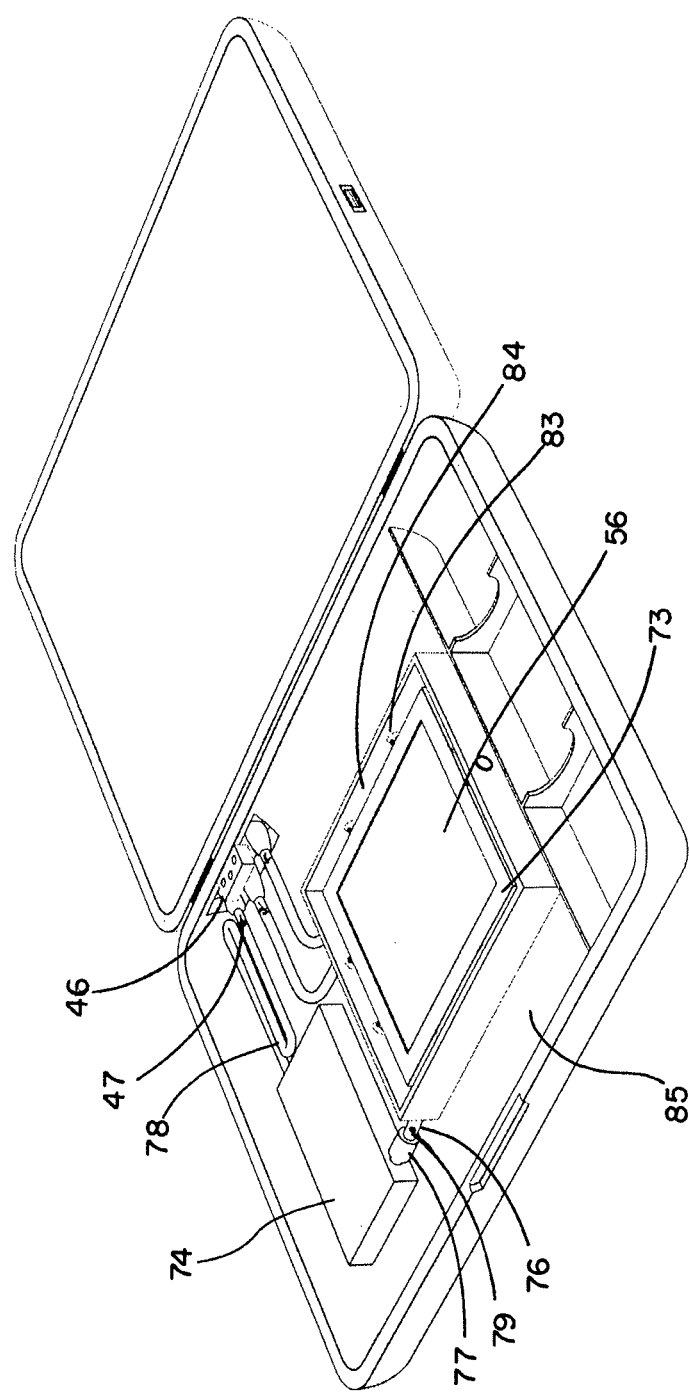
FIG. 10 is a perspective of an open carrying case showing the multicore cooling system in the bottom of the case.
Figure 11:
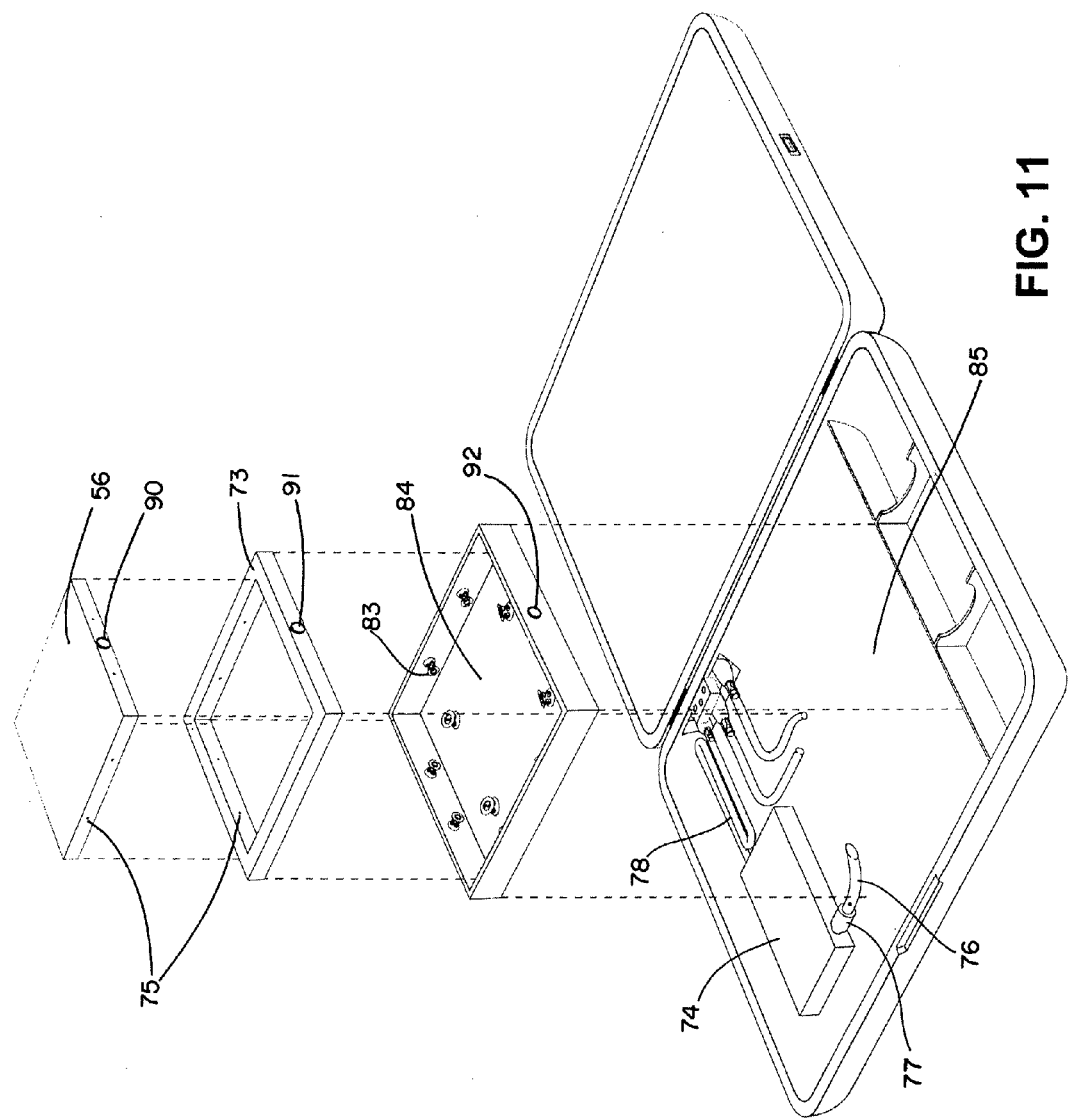
FIG. 11 is an exploded view of the components of the cooling system in the carrying case, in the bottom part of the case.

Referring now to FIG. 10, the case is cooled by a multicore system, an inner core 56 and an outer core 73. Movement of coolant (liquid nitrogen for example) is through the inner core 56 and outer core 73, to an overflow pressure tank 74 and out the exhaust 46. An exploded view of the cooling system is shown in FIG. 11.

The inner core 56, located in the case to be under the graft-containing pouch, is constructed of a thermoconductive material. The inner core is overlaid with a widely spread reinforcing Kevlar fiber net that has been soaked in thermoconductive materials such as, for example, resin or silicone gel (not shown). The inner core surface is in direct contact with the thermoconductive bottom part of the graft pouch, as shown in FIGS. 5 and 9, for maximum heat exchange.

The multi core cooling system is filled with a coolant, such as liquid nitrogen through the inlet port 42 with the one-way valve 43 (FIGS. 2 and 3). The valve opens during charging from mechanical pressure excited by the fill pipe.

Figure 12:
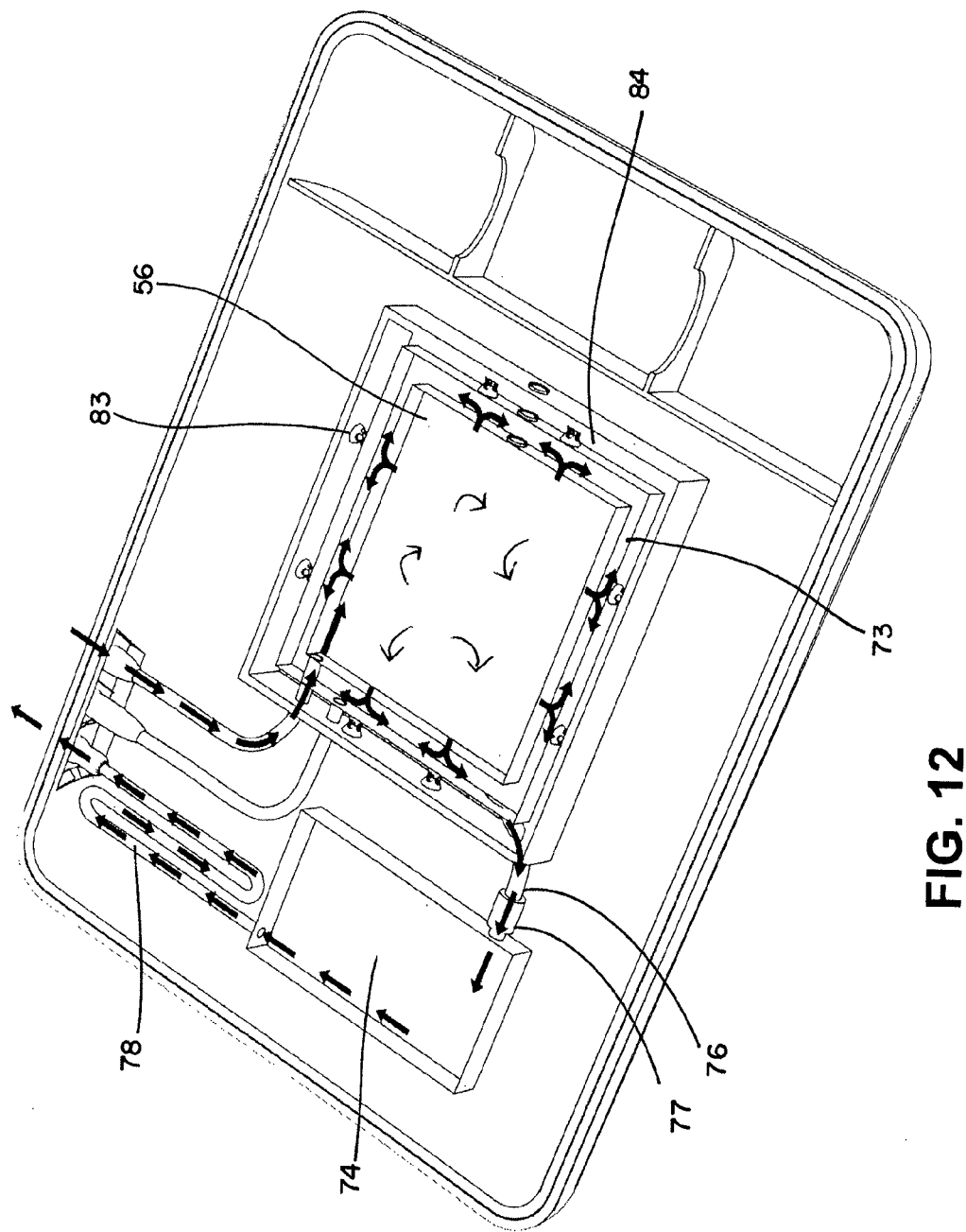
FIG. 12 is a perspective of the bottom of the carrying case showing movement of nitrogen in the cooling system as the system is filled.

The filling process is illustrated in FIG. 12. As the liquid coolant (arrow) enters the room temperature inner core 56, it boils and is vaporized. As a result, the pressure in the inner core increases, causing the gas to pass through tiny flow rate-limited pressure equalizer microports (FIG. 11, 75) into the outer core 73. The outer core 73 is a ring-like structure surrounding the inner core. This release of the warmer vapor into the outer core aids in cooling the inner core 56 as gas fills the outer core 73. But, the rate-limited flow through the microports 75 keeps the nitrogen in the inner core under pressure and in liquid form.

The gas then passes from the outer core into a pipe 76, through a double function thermo-insulated solenoid 77, into an overflow tank 74. The gas builds up in the overflow tank 74 and an outlet serpentine pipe 78. The flow out the pipe 78 is limited by the adjustable pressure regulation exhaust valve 47 (FIG. 10). This exhaust valve 47 determines the amount of residual pressure permitted in the post-solenoid part of the system.

An important part of the function of the cryogenic communicating carrying case is a microcontrolled solenoid 77. Because the resistance and the amount of power required to open the solenoid 77 is determined by the gas pressure on either side of the solenoid valve 77. This valve can also act as a pressure sensor, giving information back to the microcontroller. The microcontroller ensures that while the cooling system of the case is charging and vapor escapes via the overflow tank the same amount is added to the inner core 56 until the inner core is full of liquid low boiling point fluid like nitrogen for example. Because the solenoid operates electromagnetically, there is no direct connection between the moving components and the internal environment of the bottom of the case. Freezing or ice buildup, preventing effective function, is unlikely.

Once the cooling system is charged, the microcontroller stops energizing the solenoid 77, which causes it to close. The liquid state of the cooling fluid in the inner core 56 is then maintained by pressure.

In order to cool down the case for use, and maintain a user-set temperature, a temperature sensor 79 (FIG. 10) is located on the pipe near the solenoid 77. The temperature sensor transmits data to a microcontroller, which compares it to a set value. If the temperature is out of range, the microcontroller energizes the solenoid so that it opens and some of the coolant is allowed to flow into the overflow tank 74. As the pressure in the inner core decreases, the liquid coolant boils, absorbs heat from its surroundings, and the inner and outer core cool. The escaping coolant gas leaves the overflow tank by the serpentine pipe 78, absorbing maximum heat from the case, to the adjustable one-way mechanical valve 47 and exhausts at outlet 46. Since the valve 47 controls the pressure in the overflow tank 74, it can be adjusted for differently-sized devices or other modifications of the system.

Figure 13:
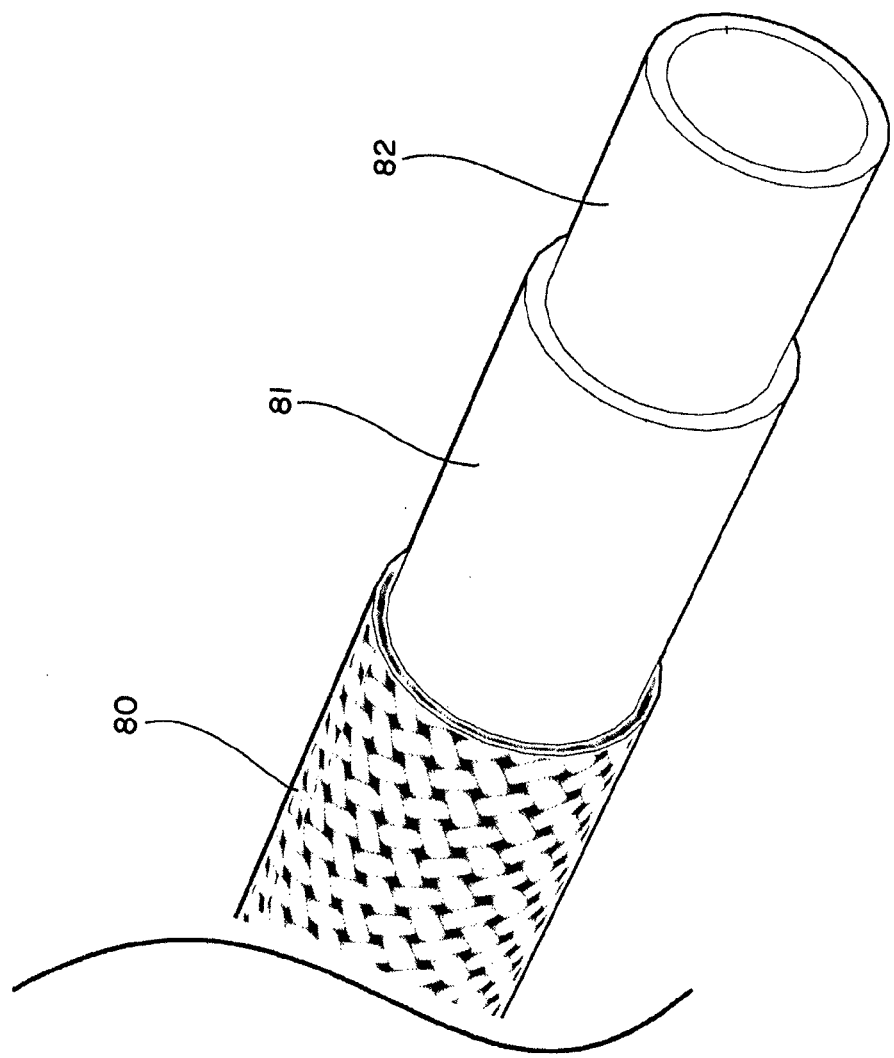
FIG. 13 is a schematic illustration of a pipe used in the carrying case showing the multilayered construction.

For strength and insulation purposes, multilayer pipes (FIG. 13) are used in the cooling system. The pipes contain a braided Kevlar outer layer 80 for strength. A thermoinsulation layer 81, made of graphite is used under the outer layer. A low-conducting, non-corroding ceramic or doped non-thermoconductive zirconium layer 82 is used as the inner layer.

Non-thermoconductive bushings 83 (FIGS. 10, 11) that support the sides of the outer core 73 and the base of the inner core 56, the vacuum core 84 that provides additional thermoinsulation, and the outer thermal insulation foam zone 85, is an important safety feature of the case, as will be described hereinafter.

Figure 14:
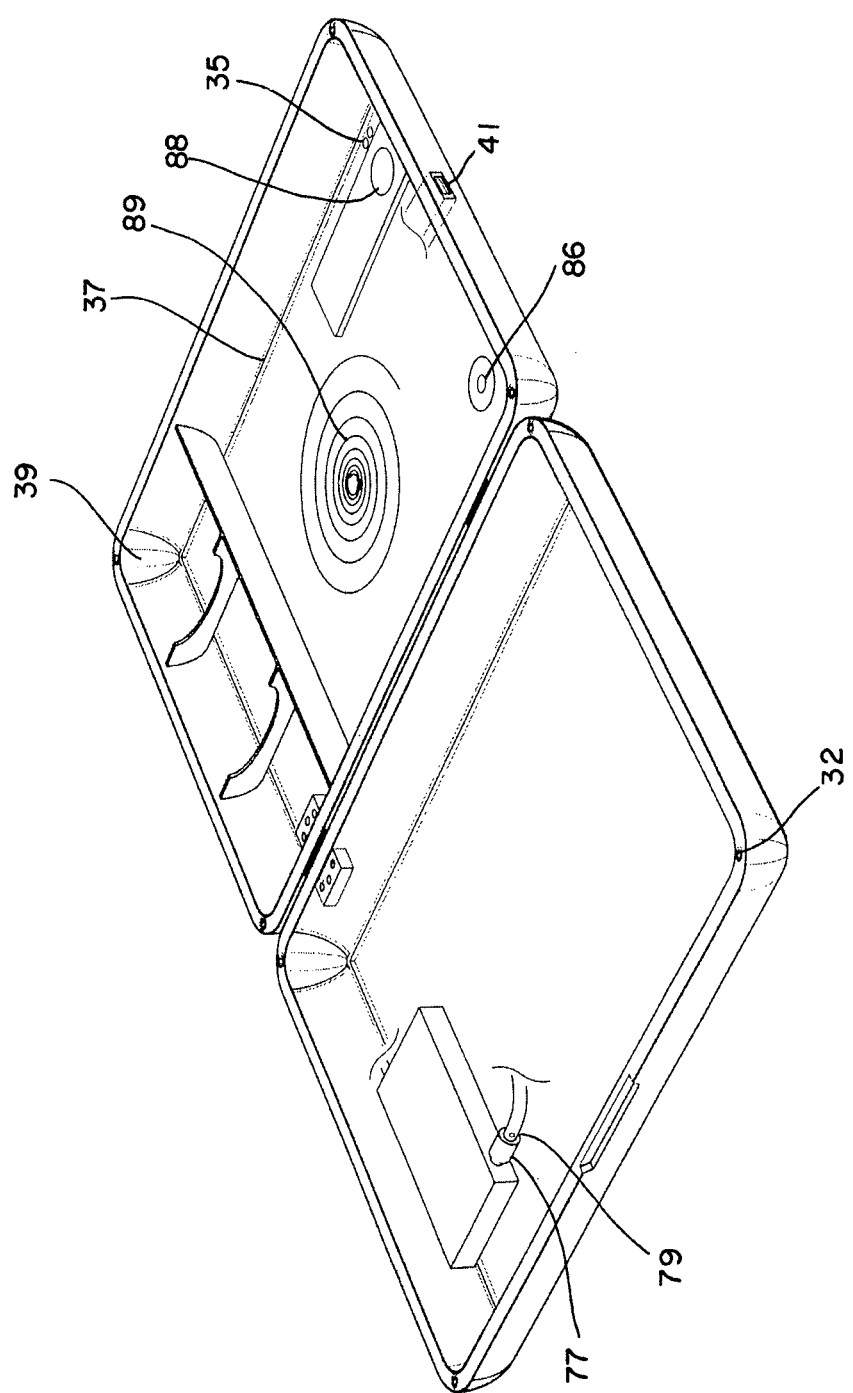
FIG. 14 is a perspective of the open case with the plates removed from the top, showing internal electrical components.
Figure 15:
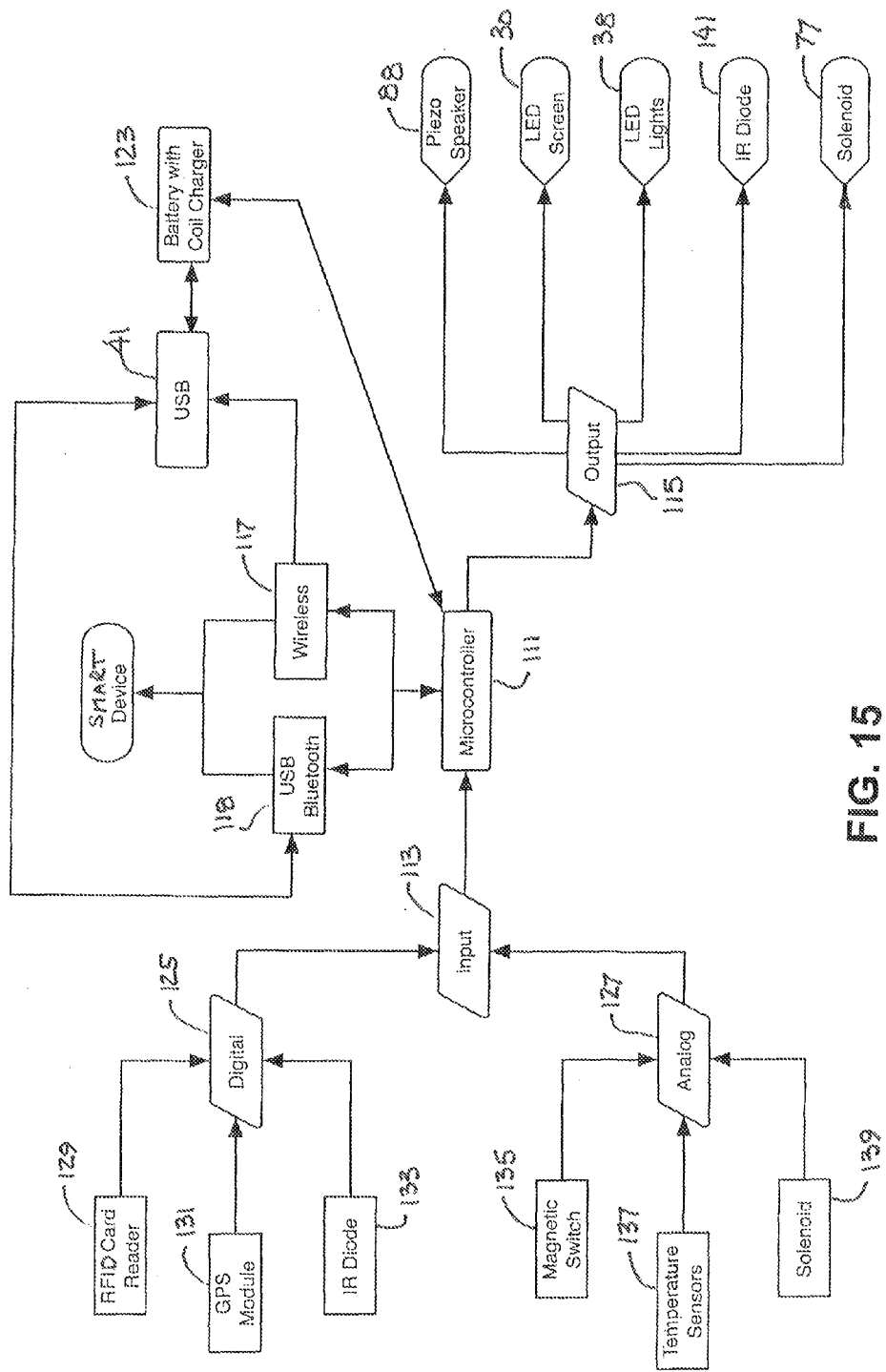
FIG. 15 is a schematic representation of a microcontroller system with a power source and multiple inputs and outputs, with the outputs coupled to multiple peripheral components.

The majority of the electronic components of the cryogenic communicating carrying case are located directly under the outer surface of the top of the case, as shown in FIG. 14. The main component is a printed circuit board (PCB) assembly (not shown), which is located below the screen 30 (FIG. 1) in the top. This includes a microcontroller 111 with various analog 127 and digital inputs 125 and outputs 115. The microcontroller 111 receives information from peripherals located throughout the case. The microcontroller outputs are assigned to regulate the function of the case and interact with the peripherals. A schematic of the microcontroller and its various inputs and outputs is illustrated in FIG. 15 and is described hereinafter.

The PCB with microcontroller 111 supports USB 41 so that various modules such as Blue Tooth® 118, Wifi® 117 and GPS®, can be added. The WiFi 117, similarly, allows the case to transmit information and receive commands. The infrared (IR) transmitting 141 and receiving diodes 133 establish connections with IR capable devices and with other cases in the vicinity. In a preferred embodiment, Blue Tooth® 118 establishes connection and pairs the case with Blue Tooth® enabled devices such as Android® phones 119, iPads® and some laptops. Compatibility with the phones, like the Android® make it simpler for the operator to create applications because the software is open source. However, the microprocessor 111 in the case has internal memory so it can be programmed to perform all the required functions independently without the assistance of an external device. The USB 41, Blue Tooth® 118, WiFi 117, and IR modules 133, 141 allow the case to communicate with other cases and devices. This way one case can transmit information to another.

The cryogenic communicating carrying case gathers information about its contents and surroundings through a system of sensors as shown in FIG. 14. First, the radio identification hardware, or frequency identification device (RFID) 129, is part of the double coil 86 (FIG. 14) that allows the user and/or cargo to scan in/be scanned in so the case displays appropriate settings. As mentioned above, a magnetic switch 32 on the front right of the case coupled with corresponding permanent earth magnets on the top and bottom of the case determines whether it is open or closed. In a preferred embodiment, the case has two temperature sensors. One is attached to the tubing in front of the solenoid 77 and monitors the temperature of the coolant before it passes the solenoid 56. The other sensor 87 is close to the outer surface of the case and monitors ambient temperature (FIG. 1).

The cryogenic carrying case contains an array of audio visual aids that can be set to user preference. A triple color high power LED surface mounted diode 38 (FIG. 1) is at one corner of the top that enables it to display colors on the four corners of the case via the fiberoptic strip 37 and reflectors 39 at the other three corners of the case. This allows the case to visually interact with the user about whether it contains an unused graft (green), the graft is expired (yellow) or the case is experiencing unusual pressure (red). Additional information, such as the temperature of the core, the date, the cargo, and the time left, is available via the LED display 30, which is constructed of multiple LEDs and a thermos-insulating backing. The LED display 30 has a Piezo speaker 88 (FIG. 14) fixed to the back that allows for audio communication by producing different frequency noises to alert a user or emit a warning.

The cryogenic communicating carrying case uses a charging coil that is connected to a lithium ion battery with charger 89 (FIG. 14). The battery can also be charged through the USB socket 41. The top of the case contains a double coil 86 (FIG. 14) that allows communication between the top and bottom of the case.

The microcontrolled double function solenoid 77 opens and closes based on readings from the temperature sensors 137 in combination with software that allows the user to vary the range within which the microcontroller will activate the solenoid to open, allowing some high pressure coolant vapor to escape. The solenoid 77 also acts as a pressure sensor because the amount of pressure in the inner core is proportional to the amount of power needed by the solenoid 77 to open it. The microcontroller can sense this change in terms of current and resistance and integrate this information with the information received from peripherals, such as the temperature sensors. This enables the microcontroller to estimate the amount of coolant remaining in the case and the number of hours the case has left.

Figure 16:
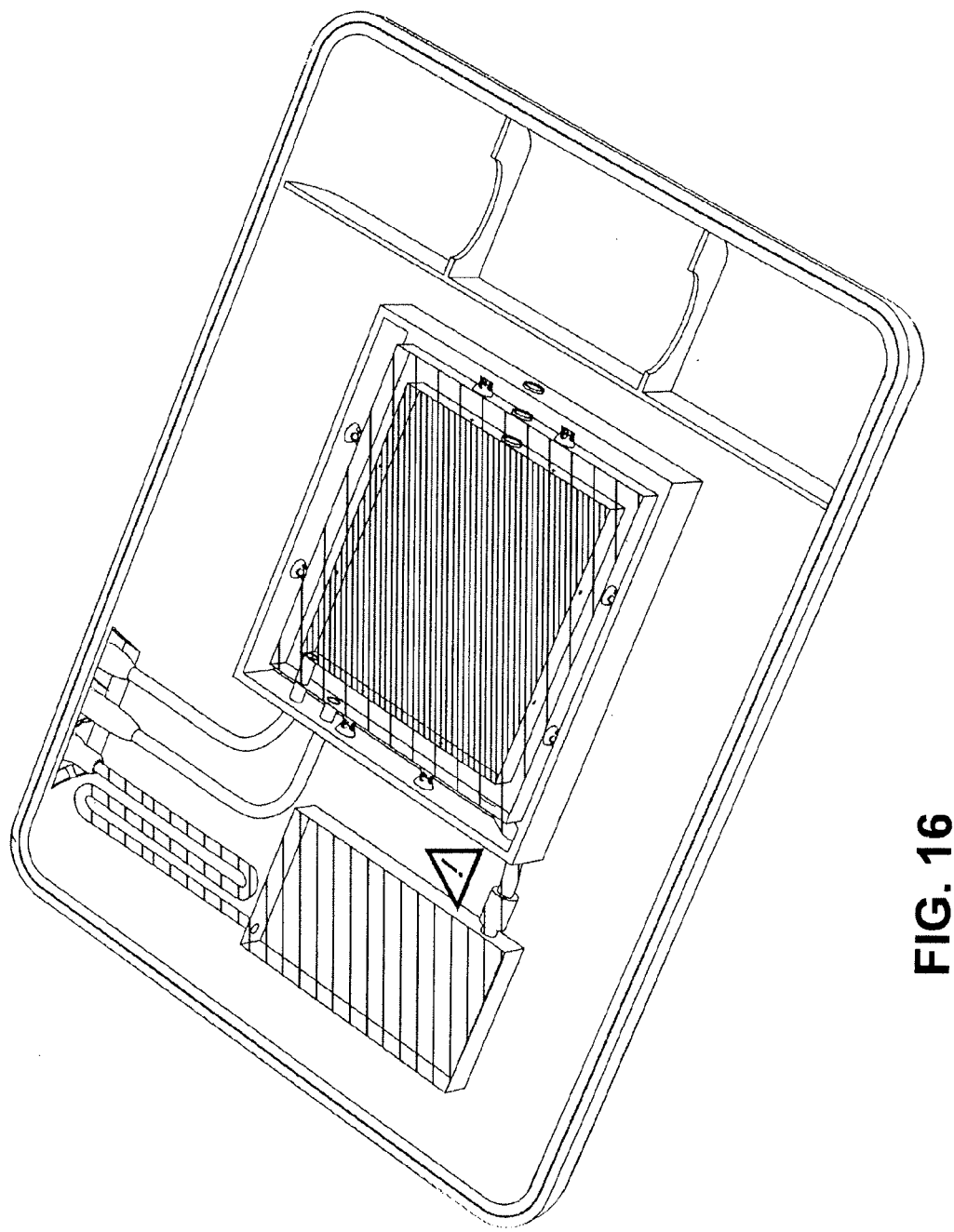
FIG. 16 is a perspective of the bottom of the carrying case showing activation of the emergency pressure release system when there is an unacceptable amount of pressure in the inner and outer cores of the system.
Figure 17:
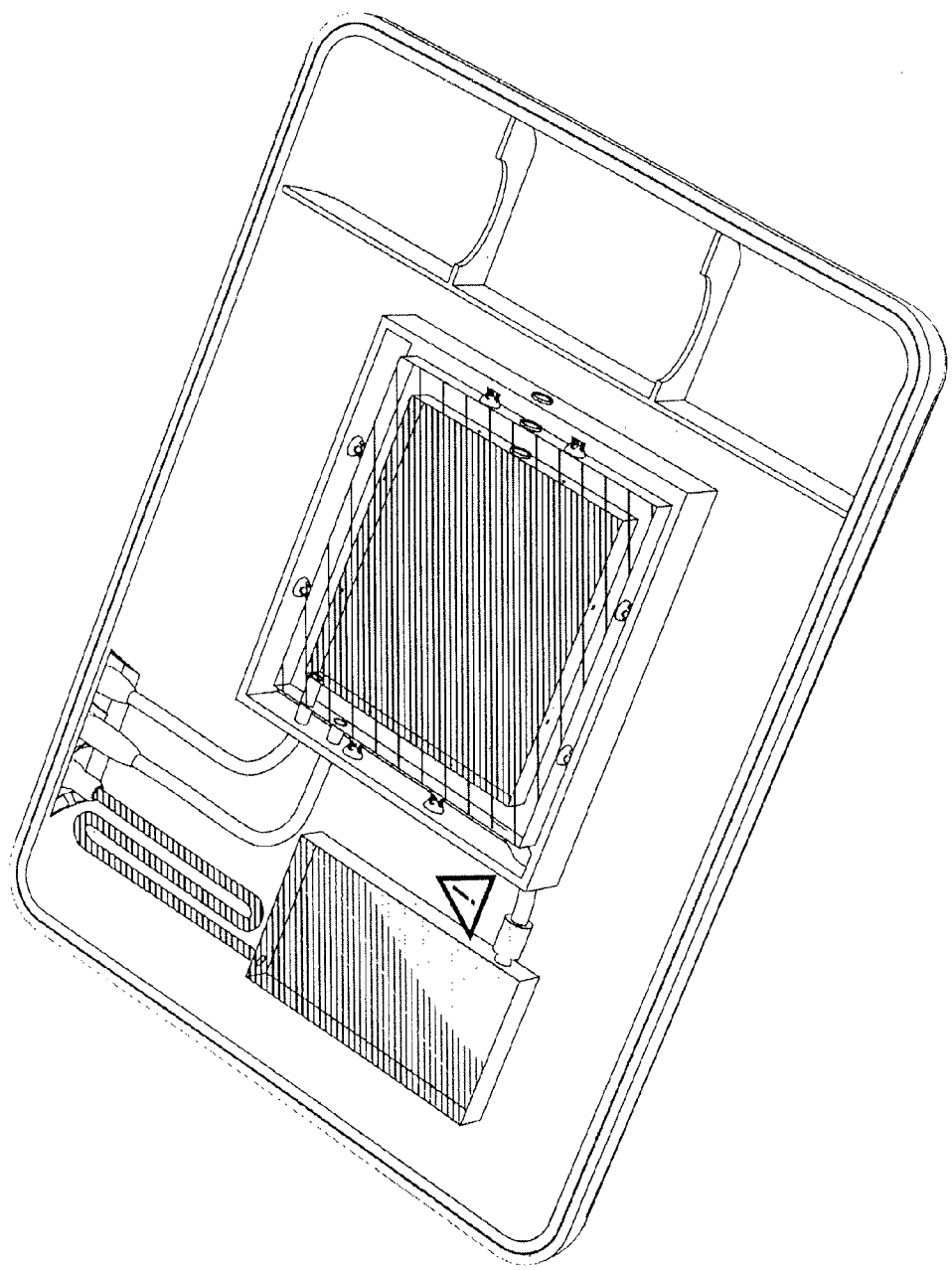
FIG. 17 is a perspective of the bottom of the carrying case showing the next stage in the emergency pressure release system, allowing the excess nitrogen gas to pass into an overflow chamber.

Because of the risks inherent in using low boiling point liquids converted to gases, a system of safety measures is integrated into the cryogenic communicating carrying case. First, if the core system of the case is exposed to extreme heat, the liquid nitrogen will boil and, as a result, increased vapor pressure is created. The solenoid valve 77 will sense the increased pressure as shown in FIG. 16. When a predetermined range or threshold is reached, the microprocessor will cause the solenoid to be energized into a continuously open position, allowing gas to evacuate and causing pressure to build up in the overflow chamber, lowering the pressure before the valve, as shown in FIG. 17. Excess pressure sensed by the solenoid 77 will trigger audio and visual alarms so the user is warned. The excess gas escapes into the serpentine pipe where it encounters the flow limited pressure regulated one way exhaust valve and is vented at a low fixed rate through the exhaust vent.

Figure 18:
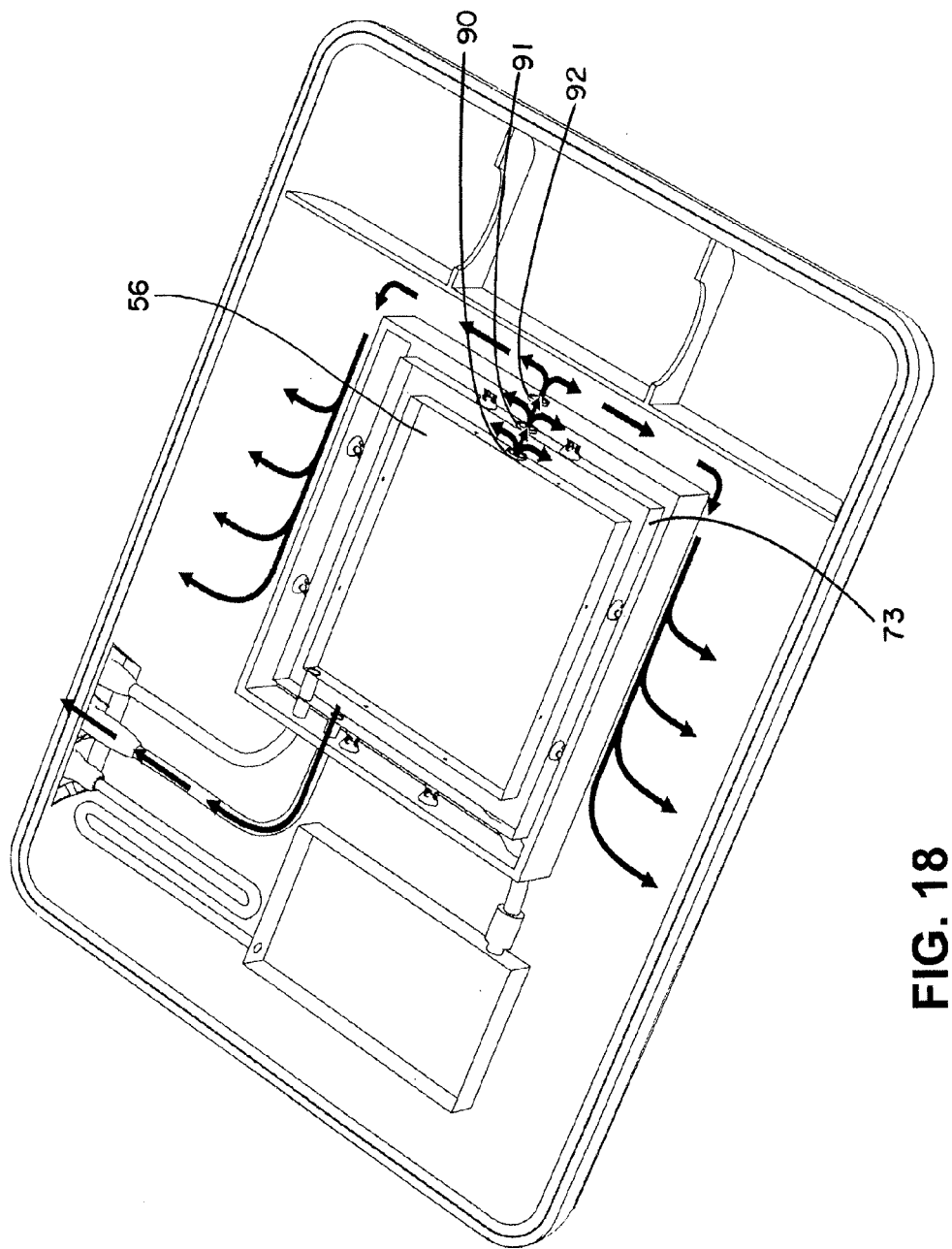
FIG. 18 is a perspective of the bottom of the carrying case showing how the build-up of nitrogen pressure causes failure of the inner and then outer core break caps, followed by nitrogen leakage into the vacuum core of the case.

If the flow rate exceeds the maximum permitted by this valve, the gas will back up via the solenoid 77 and into the outer and inner core. When the pressure reaches the pre-set fail point of the cores, the case is compromised so that it is no longer useable. At ultrahigh pressures (FIG. 18), the inner core 56 and outer core 73 break caps 90, 91 that will give way. The vacuum core 84 will absorb some of the escaping gas, redistributing the excess pressure throughout the interior of the core. Next, the vacuum core break cap 92 will fail and the remaining liquid coolant will enter the thermal insulation foam, which will act as a crumble foam area to absorb the initial force (FIG. 18). Finally, the gas may escape at the junction between the plates and the shells and the gas will harmlessly dissipate into the atmosphere.

In summary, the invention is a portable reusable cryogenic communicating carrying case for the transport, storage and use of temperature-sensitive materials. The case is capable of maintaining very low temperatures for extended periods of time while continuously monitoring and regulating the temperature of the biomaterial. It also gathers data such as a real time record of how old the biomaterial is and the state of the biomaterial, preventing use of cells with age-related diminished viability. Of course, it is entirely possible that the main benefit of biomaterial grafts consists in the secretion of growth factors, cytokines, and angiogenic factors. Again, the controlled environment provided by the case will guarantee that these biological agents remain active until the implant is placed and that the cells continue making them for as long as possible. The invention allows real time close monitoring of a biomaterial. It is possible to track immunologically distinct lines. These can be matched with the MHC profiles of individual patients, much as blood typing is today, thereby increasing the length of time that the cells will be viable, increasing the likelihood of success of graft procedures. From the moment the biomaterial is produced and placed in the device until the time it is sited on or in a patient, this invention will ensure that it is in a sealed, sterile container, kept at a constant temperature, monitored for temperature, location, and who performed the task, and the data are transmitted and made available to the distributor and end-user upon demand. The case benefits the patient, the medical facility, and the biomaterial producers. It is even environmentally friendly, being entirely re-usable.

In addition, the case can easily be modified for transport and storage of other temperature sensitive biologics, including blood, vaccines, viruses, sperm, for example. It can also be modified for nonbiologics.

What is claimed is:

1. A case for maintaining biomaterials at predetermined cryogenic temperatures, comprising:
   a top, bottom and sides forming an enclosure;
   an inner core of thermoconductive material having a top, bottom and sides for containing a liquid coolant located in the enclosure;
   an outer core ring surrounding a portion of the inner core, connected for allowing liquid coolant flow between the outer core ring and the inner core through microports located on the inner core and outer core ring;
   a vacuum core surrounding the outer core ring and the bottom of the inner core for providing a thermal barrier;
   a partially pressurized overflow tank located in the enclosure; and
   a solenoid valve connected between the outer core ring and the overflow tank by a pipe, the solenoid valve regulating coolant flow from the outer core ring into the overflow tank and sensing coolant pressure.

2. The case of claim 1 wherein the coolant is liquid nitrogen.

3. The case of claim 1 further comprising an adjustable flow limiting valve in coolant flow communication with the overflow tank for limiting the amount of coolant flow out of the tank.

4. The case of claim 1 wherein the top and bottom of the enclosure are made of non-thermoconductive material.

5. The case of claim 1 wherein the pipe connecting the outer core ring and overflow tank is a multilayer thermoinsulated, pressure pipe.

6. The case of claim 1 further comprising a removable pouch, for containing the biomaterial, having a thermoconductive coating on the one side that comes in contact with the inner core.

7. The case of claim 1 further comprising a microprocessor in the enclosure responsive to temperature signals from a temperature sensor between the outer core ring and overflow tank for controlling the solenoid valve thereby controlling coolant pressure and temperature in the cores.

8. The case for maintaining biomaterials of claim 1 further comprising a temperature sensitive material on the outside of the top or bottom of the enclosure for indicating when the case enclosure has been exposed to a predetermined heat level.

9. The case for maintaining biomaterials of claim 1 further comprising break caps on the inner core and outer core ring that open when pressure inside the cores exceed a predetermined pressure.

* * * * *